United States Patent [19]

Moret et al.

[11] 4,184,196
[45] Jan. 15, 1980

[54] DIAGNOSTIC LAMP, PARTICULARLY FOR CHECKING TEETH

[76] Inventors: Michel A. Moret, 24, rue des Vollandes, 1225 Chene Bourg; Philippe G. E. Woog, Villa "Le Sequoia" Chemin Botterel, 1222 Vesenaz, both of Switzerland

[21] Appl. No.: 744,751

[22] Filed: Nov. 24, 1976

[30] Foreign Application Priority Data

Nov. 28, 1975 [CH] Switzerland ............... 15444/75
Jun. 30, 1976 [CH] Switzerland ............... 8334/76

[51] Int. Cl.$^2$ .................................................. A61B 1/06
[52] U.S. Cl. ........................................ 433/29; 362/138; 362/260; 362/804; 433/31; 433/89
[58] Field of Search ............... 240/41.15, 2.18, 6.4 R, 240/6.45 R, 10.6 R; 128/208, 22, 21, 23; 32/69, DIG. 7, 40 R; 362/2, 34, 84, 96, 804, 119, 136, 138, 139, 230, 260

[56] References Cited

U.S. PATENT DOCUMENTS

| | | | |
|---|---|---|---|
| 1,647,862 | 11/1927 | Gaillard | 32/69 |
| 1,746,810 | 2/1930 | Anderson | 240/6.45 R |
| 1,889,143 | 11/1932 | Hirsh | 362/155 |
| 1,986,086 | 1/1935 | Weiss | 240/6.4 R |
| 2,943,184 | 6/1960 | Christopherson | 362/139 |
| 3,711,700 | 1/1973 | Westlund et al. | 128/22 |
| 3,716,170 | 2/1973 | Mangels | 240/6.4 R |
| 3,732,416 | 5/1973 | Audesse et al. | 362/260 |
| 3,806,724 | 4/1974 | Tanner et al. | 362/189 |

Primary Examiner—J. D. Miller
Assistant Examiner—Peter S. Wong
Attorney, Agent, or Firm—Kane, Dalsimer, Kane, Sullivan and Kurucz

[57] ABSTRACT

A diagnostic lamp is provided for fluorescent excitation of a fluorescible material applied to the parts of the body to be tested, in particular the teeth and gums. The lamp is battery operated and in accordance with a disclosed embodiment the light source may be at least one ligth-emitting diode capable of emitting light in a narrow range of wave lengths. A dispenser may be mounted with the lamp for containing the fluorescible material.

14 Claims, 12 Drawing Figures

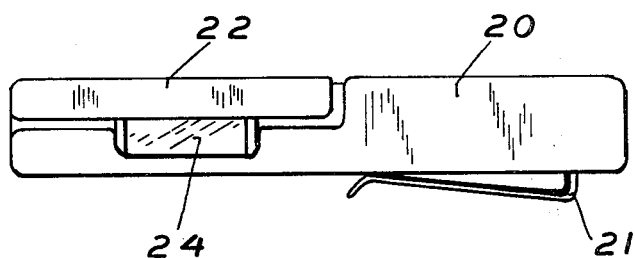
FIG. 4
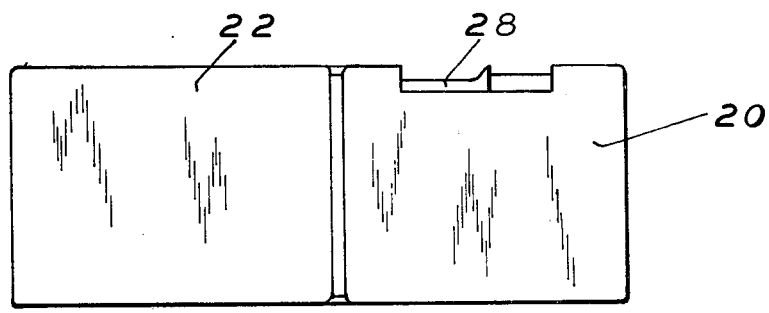
FIG. 5
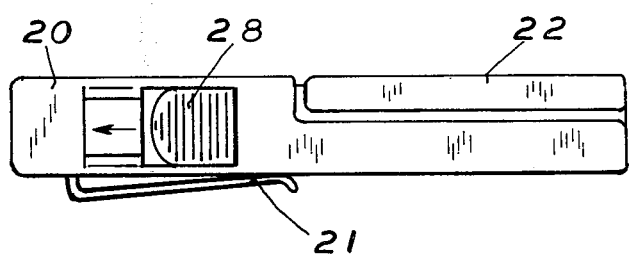
FIG. 7
FIG. 8
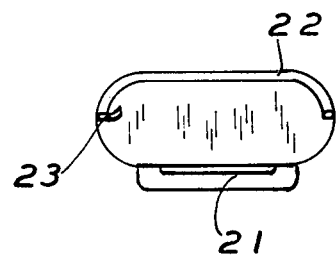
FIG. 6
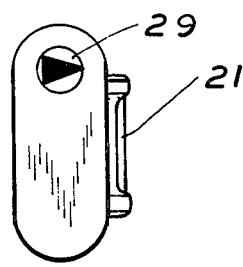

DIAGNOSTIC LAMP, PARTICULARLY FOR CHECKING TEETH

BACKGROUND OF THE INVENTION

In dental therapy, it is known and customarily the practice to make plaque easily distinguishable by painting a fluorescible solution on the teeth and then exciting it to fluorescent radiation by means of suitable lamps. Plaque is the coating on the teeth which consists mainly of bacteria and causes disease of the teeth and gums, and normally is invisible. It has been shown that fluorescible material only or at least preferably remains adhered to the plaque, but not to the clean and healthy teeth and parts of the teeth. The same goes for those parts on which tartar has formed by mineralization of the plaque or which already have been attacked by dental decay. Thus, these critical or respectively diseased parts of the teeth may in a simple manner be made visible and located by the foregoing checking treatment and procedure, since only these parts fluoresce under illumination and hence are brought into sharp relief against the other non-fluorescent regions. In addition, by the fluorescent effect, diseased places on the gums as well as other diseased regions of skin and tissue can also be made visible.

A test lamp has been proposed for the purpose described and utilizes an incandescent lamp as light source, together with a dichroic reflector behind the lamp and a dichroic filter in front of the lamp as well as preferably another dichroic observation mirror which has the same transmission and reflection characteristics as the filter. In that way the radiation available for illumination of the parts to be tested is restricted essentially to blue light which particularly excites a fluorescin solution; and, as far as possible, only a little radiation is emitted having those wave lengths which correspond with the color of the yellow or green fluorescent radiation. Only in this manner can a significant contrast be achieved between the fluorescing regions and their non-fluorescing surroundings. Otherwise the non-fluorescing surroundings under illumination with the light of the fluorescent radiation would appear approximately of the same hue as the latter.

The known test-lamp is costly to produce and consequently is relatively expensive. It is complicated in construction and also troublesome to handle. Furthermore, the user must always be concerned that the fluorescent material too, which is indispensable and normally in liquid form, is always handily available. For these reasons the test-lamp does not fulfill those prerequisites which would favor an otherwise wide distribution amongst the consuming public interested in oral hygiene and regular self-checking of the condition of the mouth particularly teeth and gums.

SUMMARY OF THE INVENTION

The object of the invention is to provide a diagnostic lamp for the stated purposes, which is simply constructed and can be produced inexpensively, can be handled easily and conveniently by the user and requires no superfluous manipulation and hence can be applied without problems to preventive checking of teeth by regular self-observation.

A diagnostic lamp of this invention is a battery-operated pocket-lamp on which a dispenser for the fluorescent material is arranged interchangeably.

It has been found that a comparatively simply constructed pocket-lamp is adequate, the light from which exhibits wave lengths shorter than those of the fluorescent radiation to be excited. In addition, the light does not for all practical purposes, or to such a slight degree, contain the color of the spectral range of this fluorescent radiation. Thus, there is more than adequate contrast between the excited fluorescent light and the non-fluorescing surroundings illuminated by the lamp. For that purpose, it is of particular significance that it is sufficient to equip the pocket lamp with a normal incandescent lamp of adequate brightness and with a filter adapted to the fluorescent material to be employed in such a way that the exciting radiation necessary to the generation of the fluorescence is transmitted in adequate strength and the spectral range of the fluorescent radiation itself is adequately absorbed. Thus, in the case of the employment of, for example, fluorescein as the fluorescible solution which emits green fluorescent light, just one filter may be employed which essentially absorbs green light and adequately transmits blue light. If eosin is employed as the solution the filter must essentially transmit the exciting green light and absorb in the yellow-orange range of the emitted fluorescent radiation. The filter may also be simply the correspondingly colored incandescent bulb itself.

The dispenser for the fluorescible material is arranged directly on the housing of the pocket lamp and hence always conveniently handy. Accordingly, its presence facilitates for the user the application of the diagnostic lamp and speeds up the diagnostic inspection. Preferably the dispenser consists of a spray container in the shape of a small tube which can be inserted replaceably inside the housing of the pocket lamp in an appropriately adapted cavity adjacent the battery or batteries and projects with its spray nozzle from the housing at a suitable point.

In order to permit self-checking of the teeth by the diagnostic lamp of this invention, a mirror may be attached to the housing of the pocket lamp. This mirror may be collapsed inwardly when not in use and folded outwardly to its operating position at which, upon illuminating the teeth with the pocket lamp, permits the user observation of his teeth directly. Advantageously, this mirror may be placed at the exact setting of the angle of view while at the same time be mounted rotatably on the housing of the pocket lamp.

In accordance with a further preferred embodiment, the dispenser may be a cartridge similar to that employed for refilling fountain pens. This type of dispenser includes a dropper and a compressible flexible wall. It may be arranged as an insert removable from the housing, which also receives the batteries. In this connection a slide is fitted to the outside of the housing which upon actuation first of all slides to the outside of the housing which upon actuation first of all slides the cartridge by its head out through an appropriate opening in the housing and then squeezes the flexible zone of the wall appropriately for the purpose of delivering one drop at the head of the cartridge. In this embodiment, the housing of the pocket lamp may preferably be made rectangular and have a hinged cover which in the closed state covers the incandescent lamp and on the inside of which a mirror is arranged; moreover, this cover advantageously cooperates with the on-off switch of the pocket lamp in such a way that with the cover cl ;ed the pocket lamp is switched off and with the cover open it is switched on.

It is likewise important in a particular application of this invention that the test lamp emit as far as possible no ultraviolet radiation, that is, not only for health reasons but also because under ultraviolet radiation experience is that sound clean teeth as well as also certain artificial teeth or tooth crowns fluoresce, which would again impair the desired checking effect or makes it quite ineffective.

BRIEF DESCRIPTION OF THE DRAWINGS

In the drawings;

FIG. 4 is a side elevational view of another embodiment of a diagnostic lamp incorporating the teachings of this invention with the cover closed;

FIG. 5 is a top plan view thereof;

FIG. 6 is an end view thereof;

FIG. 7 is an elevation of the side opposite that appearing in FIG. 4;

FIG. 8 is a view of the end opposite that appearing in FIG. 6;

DETAILED DESCRIPTION

Figure 1:
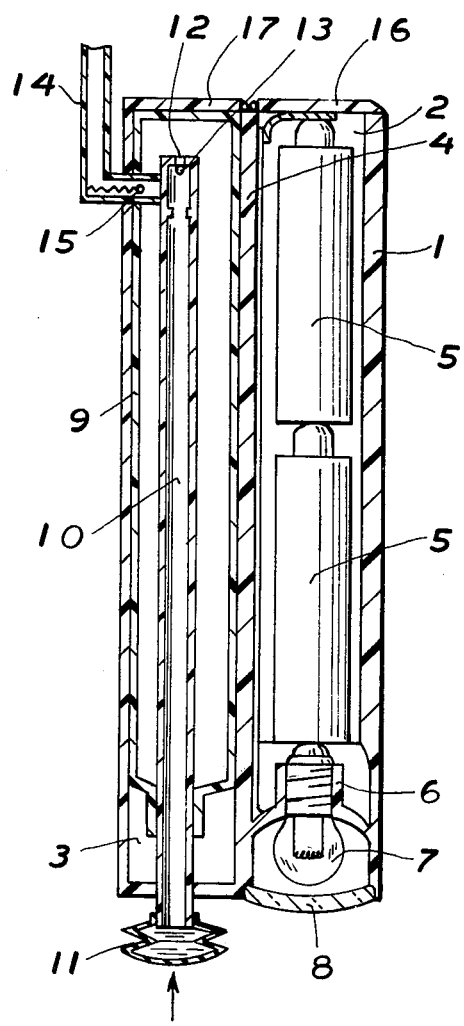
FIG. 1 is a longitudinal section view through an embodiment of a diagnostic lamp in accordance with the invention.

The pocket lamp illustrated in the Figures has an elongated housing 1 having two cavities 2 and 3 lying side by side, separated by a partition 4 and extending in each case in the longitudinal direction. The one cavity 2 is used for receiving two electric batteries 5 connected one behind the other, and at its front end, is mounted in a conventional manner a socket 6 containing an incandescent bulb 7 held in it. A filter 8 is disposed in front of the incandescent bulb 7.

The other cavity 3 in the housing 1 of the pocket lamp contains a pipelike or tubelike dispenser 9 of fluorescible solution. This dispenser 9 is provided with a small central immersion-tube 10 which projects out of the front of the housing 1 and is closed at that point by a resilient pushbutton 11 in the form of a resiliently compressible bellows. The inner end-face of the immersion-tube 10 has an opening 12 which can be closed by a ball-valve 13. In proximity to this opening 12 is an outlet nozzle 14 which branches from the circumferential wall of this immersion-tubelet 10, passing through the wall of the dispenser 9 and projecting out of the housing 1. The nozzle is provided with a spring-loaded discharge-valve 15 and its mouth is directed towards the rear so that it permits fluorescible solution to issue from the end of the pocket lamp opposite from the incandescent bulb 7. When the user presses on the resilient pushbutton 11 the ball-valve 13 closes the opening 12 in the immersion-tube 10 and the liquid present in this immersion-tube 10 is forced out through the outlet nozzle 14, with the ball-valve 15 opening against the action of its closing-spring. In this connection, it is sufficient to direct the outlet nozzle 14 on the back of the pocket lamp housing 1 towards the teeth to be checked or to bring it near to the teeth. Then the resilient pushbutton 11 is released to permit the flexible wall to expand because of its resilience. Suction is coated to raise the ball-valve 13 from the opening 12 and a corresponding amount of liquid is sucked into the immersion-tube 10. Projections from the inner wall of the immersion-tube 10 in front of the outlet nozzle 14 limit the degree of lift of the ball-valve 13.

Cap-covers 16 and 17 close off the two cavities 2 and 3 on the back of the housing 1 and are either hinged onto the housing as indicated in FIG. 1 or else fastened detachably by screws or a catch. The outlet-nozzle 14 advantageously projects through a longitudinal notch in the housing 1, which opens out at the back of the housing, so that after opening or removing the cap-cover 17 and after removal of the resilient pushbutton 11, the dispenser 9 may simply be taken out of the housing 1 from the back. In this way, an empty dispenser may easily be exchanged for a full dispenser. The front endwall bounding the cavity 3 may also be eliminated so that the dispenser 9 may be exchanged without the necessity of removing the resilient pushbutton 11.

Figure 2:
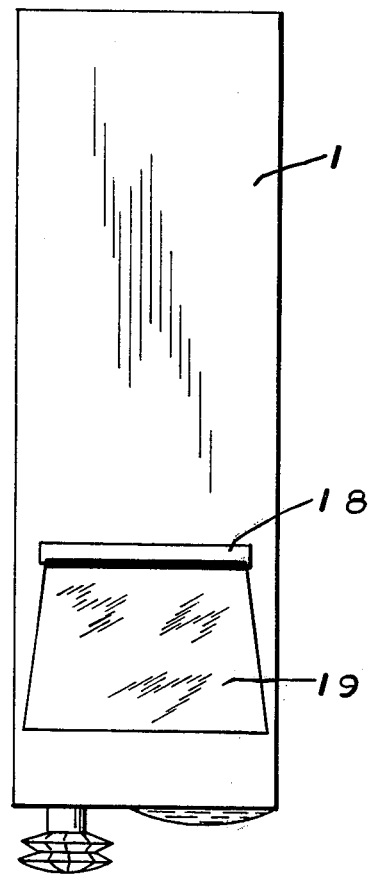
FIG. 2 is a side elevation of this diagnostic lamp.
Figure 3:
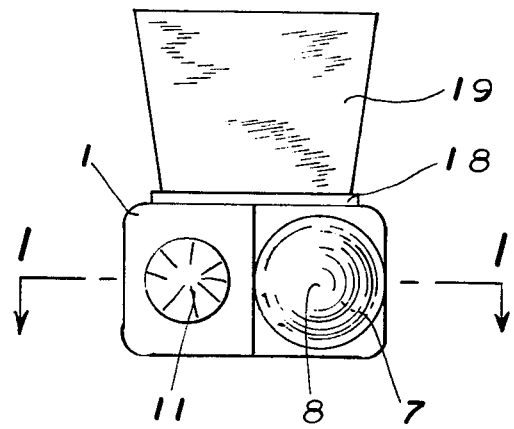
FIG. 3 is a view of the endface of the lamp, showing the incandescent bulb.

As shown in FIGS. 2 and 3, a mirror 19 is hinged onto the outside of the housing 1 by means of a hinge 8, and may be folded up out of the folded-down position as FIG. 2 into the operating position as FIG. 3. In this way, the user may observe his teeth directly by means of this mirror when he points the beam of the diagnostic lamp at them. The folded-down position of rest and the folded-up operating position of the mirror 19 are preferably snap-in positions or positions preloaded by a spring. In order to adjust the mirror with precision, provisions may be made to permit turning of the mirror on the housing about an axis perpendicular to its axis of hinge.

The optical filter 8 is related to the fluorescible solution to be used in such a way that it largely absorbs the spectral range of the excited fluorescent radiation and transmits the shorter wave lengths necessary to the excitation of the fluorescence.

Figure 9:
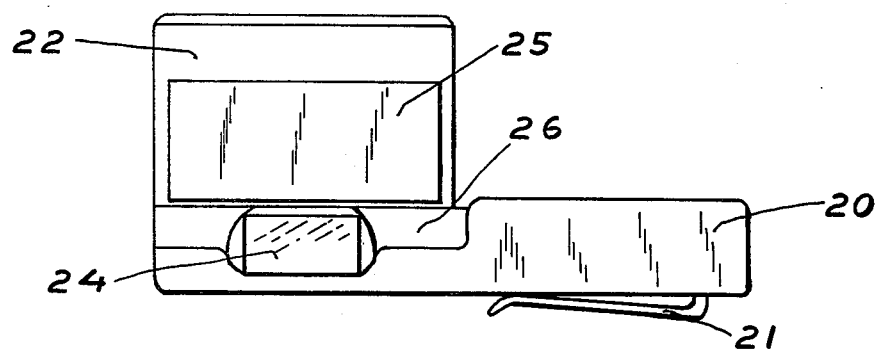
FIG. 9 is a view similar to FIG. 4 with the cover open.
Figure 10:
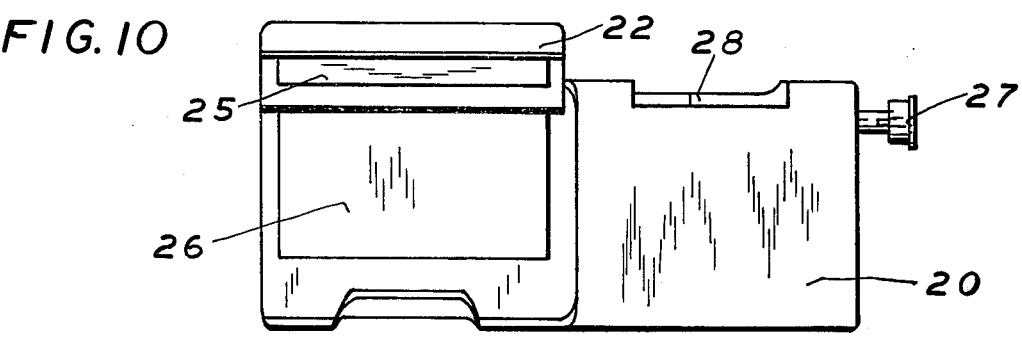
FIG. 10 is a view similar to FIG. 5 with the cover open.
Figure 11:
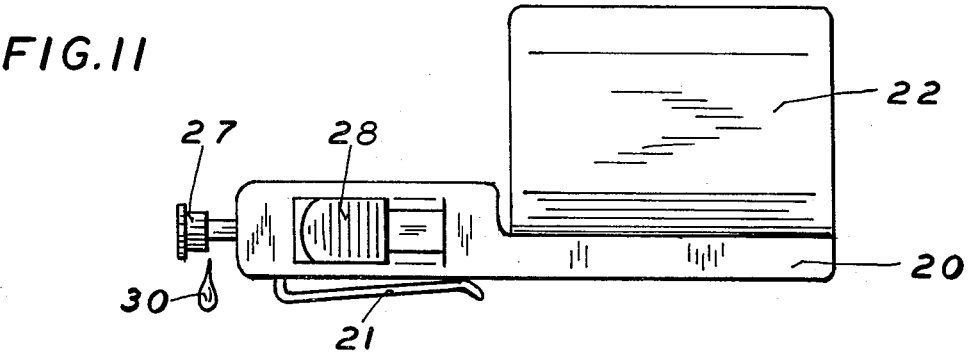
FIG. 11 is a view similar to FIG. 7 with the cover open.
Figure 12:
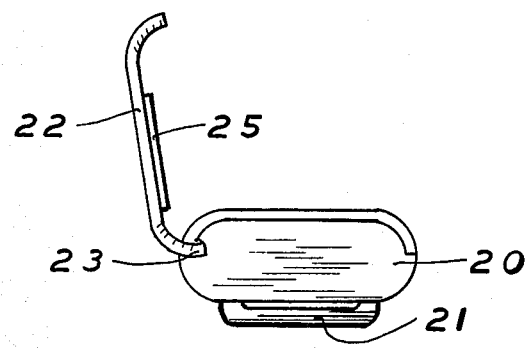
FIG. 12 is a view similar to FIG. 8 with the cover open.

The embodiment of a diagnostic lamp illustrated in FIGS. 4–12 includes an essentially rectangular flat housing 20 having a spring fastener-clip 21. Accordingly this pocket lamp may, for example, be carried in the top jacket pocket and fastened there like a pencil. According to FIGS. 6 and 8 which show views of the two opposite narrow endfaces of the pocket lamp, the long narrow sides of the housing are rounded. On the wide face of the housing forming the top, a cover 22 conforming to the shape of the housing is hinged by means of a hinge 23 but extends over only about half of the housing. The incandescent bulb 24 is arranged on the one long rounded narrow side, outside the center in such a way that in the closed state of the cover 22 as may be seen in FIG. 4, it is at least partially covered over. A mirror 25 is as illustrated in FIGS. 9 and 12, fastened to the inside of the cover, which with the cover 22 folded up lies behind and above the incandescent bulb 24 and enables the user to perform the self-check conveniently when illuminating the teeth.

The cover 22 is formed and mounted in such a way that the pocket lamp with the cover closed is switched off and with the cover open is switched on. This is most simply done by, for example, a spring-loaded on-off switch in the form of a pushbutton switch which with the cover opened is released and assumes its "on" position under the action of its spring, whilst with the cover closed it is held in its "off" position. In its closed position the cover 22 is preferably retained by a suitable catch or by a suitable resilient prestress means.

In the housing 20 a housing insert 26 is provided, which with the cover 22 opened is simply withdrawable and is equipped both for receiving the batteries and also for receiving a replaceable dispenser for the fluorescible solution. This dispenser in the example being considered consists of a cartridge in itself known, which includes a head 27 having a suitable opening as a dropper and the wall of which is made flexible over part of its area in such a way that this flexible area may be squeezed for the purpose of delivering one drop. On the narrow side of the housing 20 opposite from the incandescent bulb 24, a slide 28 is fitted next to the cover 22 to be able to slide to and fro for actuation of the dispenser cartridge. The adjoining endface of the housing 20 has according to FIG. 6, an opening 29 through which the head 27 of the dispenser cartridge may emerge.

A lug may be provided on the slide 28, which projects inside the housing against which the back wall or bottom wall of the dispenser cartridge rests under the action of the spring. This spring may embrace the inner part of the head 27 of the dispenser and could be biased at one end against the inner surface of the end of the housing 20 which includes the opening 29 and at its other end against the front wall of the actual receiver-chamber for the cartridge. When the slide 28 is pushed in the direction of the arrow as in FIG. 7 into the position shown in FIG. 11, the dispenser cartridge is carried along with the lug fastened to the slide 28 in the same direction against the action of the spring. In this manner the head 27 of the dispenser as shown in FIG. 11 emerges from the opening 29 and at the same time the flexible area of the wall of the cartridge is squeezed enough by increasing spring tension for a drop 30 of the liquid to emerge from the head 27 of the dispenser, as indicaed diagrammatically in FIG. 11. With this drop of liquid the user can conveniently moisten the regions of the teeth and gums which are to be checked, before he then performs the personal inspection or check. After release of the slide the dispenser cartridge together with the slide assume once more their original positions. The depressed and squeezed area of the cartridge wall will stretch again to resume its original position so that at the next actuation of the slide 28 a drop is again delivered. In front of the incandescent bulb 24 a suitable filter is again provided, or the incandescent bulb itself is appropriately colored.

The invention is not restricted to the disclosed embodiments, but as regards the form of the housing, the type and form of the dispenser for the fluorescible liquid as well as the fastening of it in or onto the housing may be varied greatly. Thus, in principle, the housing may also be formed in two parts so that one part of the housing accepts the dispenser and may be connected with the other lamp-part containing the batteries and the incandescent bulb, for example, by means of an elastic clamp. In a further possible embodiment, the cavity for accepting the dispenser or a fastener device holding the dispenser may also be arranged coaxially with the batteries and behind them. In the example of FIGS. 4 to 12, again, elimination of a housing insert, permits the batteries and dispenser after opening of the cover which may also extend over the whole length of the housing, to be insertable directly into the housing. In the first example of FIGS. 1-3, the folding mirror 19 like the cover 22 in the second example, may switch the lamp on when folded up and switch it off when folded down.

In accordance with another embodiment of this invention the light source emits only in one narrow range of wave lengths, which may be at least in approximation monochromatic. More especially suitable as a light source are light-emitting diodes or electroluminescent diodes, since they can be operated by a very low supply voltage of only a few volts, in particular by about 2 volts, and by very low currents of the order of magnitude of a few $10^{-2}$ amps, and they are available in very small dimensions. For the achievement of adequate light intensity, a number, e.g., 2 to 4 light-emitting diodes may be arranged side by side, such as are currently employed for light indicators in electrical apparatus, for example, in pocket computers and in electronic watches. Since these diodes are obtainable with different colors of light, the light source in the case of the lamp in accordance with the invention can by selection of the color of the light readily be adapted to the excitation curve or excitation radiation of different fluorescible materials. In the case of fluorescence of solid or liquid materials, as is well known, the incident light becomes partly absorbed and as a rule emitted again as radiation of longer wave length.

If, for example, fluorescein is employed as the fluorescible solution, which emits green fluorescent light, blue light emitting diodes are advantageously employed for excitation. Likewise in the case of an appropriate fluorescible solution green light emitting diodes can also advantageously be employed, of which, e.g., three diodes may form in the lamp in accordance with the invention a light source of adequate intensity. A diagnostic lamp, utilizing light-emitting diodes may be reduced to pocket size that is readily handy and convenient to use, troublefree and of reduced cost.

Thus, the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed is:

1. A pocket-size diagnostic lamp particularly for checking teeth by fluorescent excitation of a fluorescible material applied to the parts of the body to be tested, said lamp comprising a housing; a light source capable of exciting fluorescible material and battery means mounted by the housing for supplying electrical energy to the light source; a dispenser for the fluorescible material, the dispenser being provided with an immersion tube therein having one end which projects out of the housing, a resilient pushbutton closing the immersion tube outside the housing, the other end of the immersion tube located within the housing and having a valved opening, an outlet nozzle which branches from the immersion tube and projecting out of the housing, the nozzle being provided with a valve, whereby when the resilient pushbutton is pressed, the valved opening of the immersion tube closes and liquid is forced out through the outlet nozzle, and when the pushbutton is released, suction is created to open the valved opening of the immersion tube and suck in the fluorescible material; and mounting means for coupling the dispenser to the housing in an interchangeable manner.

2. A diagnostic lamp as described in claim 1 wherein the pushbutton is in the form of a compressible bellows.

3. A pocket-size, diagnostic lamp particularly for checking teeth, for fluorescent excitation of a fluorescible material applied to the parts of the body to be tested, in particular the teeth and gums, said lamp comprising, a housing, a light source capable of exciting fluorescible material and battery means mounted by the housing for supplying electrical energy to the light source, a dispenser for the fluorescible material, the dispenser being in the form of a cartridge having a dispenser-head including a dropper, and a wall of the cartridge being partially of a flexible compressible material, the housing having an opening through which the head is adapted to pass and a slide actuable from outside the housing which upon actuation slides the dispenser cartridge so that the head of the dispenser emerges through said opening in the housing and compresses its flexible wall for the purpose of delivery of one drop, and mounting means for coupling the dispenser to the housing in an interchangeable manner.

4. A diagnostic lamp according to claim 3, wherein the housing is approximately rectangular and includes an insert which receives the batteries and the dispenser and which is withdrawable from the housing.

5. A diagnostic lamp according to claim 4, wherein the light source is an incandescent bulb arranged along a side of the rectangular housing.

6. A pocket-size, diagnostic lamp, particularly for checking teeth, for fluorescent excitation of a fluorescible material applied to the parts of the body to be tested, in particular the teeth and gums, said lamp comprising, a housing, a light source and battery means mounted by the housing for supplying electrical energy to the light source, a dispenser for the fluorescible material, mounting means for coupling the dispenser to the housing in an interchangeable manner, and a filter mounted by the housing and matched with the fluorescible material and which transmits essentially the radiation from the incandescent bulb necessary for the fluorescent excitation and essentially absorbs the spectral range corresponding with the fluorescent light.

7. A diagnostic lamp according to claim 6, wherein the said filter is formed by the appropriately colored incandescent bulb itself.

8. A pocket-size dispenser for storing and dispensing a fluorescible material to be applied to the teeth for testing by fluorescent excitation of said material, comprising a housing, a cartridge within said housing having a dispenser-head including a dropper, a wall of said cartridge being partially of flexible compressible material, said housing having an opening through which said dispenser-head is adapted to pass, a slide actuable from outside the housing which upon actuation slides the dispenser cartridge so that the dispenser-head emerges through said opening in said housing and compresses its flexible wall for the purpose of delivering of one drop, and mounting means for coupling said cartridge to said housing in an interchangeable manner.

9. A dispenser as claimed in claim 8 further including in combination a light source mounted to said housing capable of fluorescent excitation of said fluorescible material.

10. A dispenser as claimed in claim 9 further including in combination a mirror hingedly mounted to the housing, said mirror being pivotable between a rest position folded down and a folded-up operating position at which it allows an individual to observe his illuminated teeth.

11. A pocket-size apparatus for storing and dispensing a fluorescible material to be applied to the teeth for testing by fluorescent excitation of said material, comprising a housing, a dispenser positioned within said housing, an immersion tube within said dispenser having one end which projects out of said housing, a resilient pushbutton closing said immersion tube outside said housing, the other end of said immersion tube positioned within said dispenser and having a valved opening, an outlet nozzle which branches from said immersion tube and projects out from said housing, said nozzle being provided with a valve, whereby when said resilient button is pressed, and valved opening of said immersion tube closes and liquid is forced out through said outlet nozzle, and when said pushbutton is released, suction is created to open said valved opening of said immersion tube and suck in the fluorescible material, and mounting means for coupling said dispenser to said housing in an interchangeable manner.

12. An apparatus as described in claim 11 wherein said pushbutton is in the form of a compressible bellows.

13. An apparatus as described in claim 11 further including in combination a light source mounted to said housing capable of fluorescent excitation of said fluorescible material.

14. An apparatus as described in claim 13 further including in combination a mirror hingedly mounted to said housing, said mirror being pivotable between a rest position folded down and a folded-up operating position at which it allows an individual to observe his illuminated teeth.

* * * * *

UNITED STATES PATENT AND TRADEMARK OFFICE
CERTIFICATE OF CORRECTION

PATENT NO. : 4,184,196

DATED : January 15, 1980

INVENTOR(S) : Michel Moret and Philippe Guy Woog

It is certified that error appears in the above-identified patent and that said Letters Patent are hereby corrected as shown below:

Claim 11, column 8, line 30, "and" should be --the--.

Signed and Sealed this

Twenty-eighth Day of October 1980

[SEAL]

Attest:

SIDNEY A. DIAMOND

Attesting Officer

Commissioner of Patents and Trademarks